(12) United States Patent
Cook et al.

(10) Patent No.: US 12,295,824 B2
(45) Date of Patent: May 13, 2025

(54) METHOD AND APPARATUS FOR FIXATION OF IMPLANTABLE DEVICES ADJACENT A BODY LUMEN

(71) Applicant: Uromedica, Inc., Plymouth, MN (US)

(72) Inventors: Timothy C. Cook, Wayzata, MN (US); John H. Burton, Minnetonka, MN (US)

(73) Assignee: Uromedica, Inc., Plymouth, MN (US)

( * ) Notice: Subject to any disclaimer, the term of this patent is extended or adjusted under 35 U.S.C. 154(b) by 0 days.

(21) Appl. No.: 16/532,811

(22) Filed: Aug. 6, 2019

(65) Prior Publication Data

US 2020/0022796 A1   Jan. 23, 2020

Related U.S. Application Data

(63) Continuation of application No. 15/371,591, filed on Dec. 7, 2016, now abandoned, which is a continuation of application No. 15/143,784, filed on May 2, 2016, now abandoned, which is a continuation of application No. 14/169,988, filed on Jan. 31, 2014, now abandoned, which is a continuation of application No. 12/467,257, filed on May 16, 2009, now abandoned.

(60) Provisional application No. 61/053,758, filed on May 16, 2008.

(51) Int. Cl.
*A61F 2/00* (2006.01)
*A61M 25/00* (2006.01)

(52) U.S. Cl.
CPC ............ *A61F 2/0027* (2013.01); *A61F 2/004* (2013.01); *A61F 2/0077* (2013.01); *A61M 25/0017* (2013.01); *A61F 2002/0086* (2013.01); *A61F 2250/0018* (2013.01)

(58) Field of Classification Search
CPC .......... A61M 25/0017; A61M 25/0074; A61M 25/02; A61M 25/10; A61M 25/0068; A61M 2025/0175; A61F 2/0027; A61F 2/004; A61F 2002/0086; A61F 2/0077; A61F 2250/0018; A61F 2/0036; A61F 2/005; A61F 2/0013; A61F 2/0009; A61F 2/0045; A61F 5/48; A61B 2017/0414; A61B 2017/0461; A61B 2017/0462; A61B 2017/00805; A61B 2017/044; A61B 17/0401
USPC ..................... 600/29, 30; 623/1.13
See application file for complete search history.

(56) References Cited

U.S. PATENT DOCUMENTS 5,167,614 A * 12/1992 Tessmann ................ A61F 2/92
                                                    623/1.14
5,964,806 A * 10/1999 Cook ..................... A61B 17/12
                                                    606/191
6,045,498 A    4/2000  Burton et al.
(Continued)

OTHER PUBLICATIONS

"U.S. Appl. No. 12/467,257, Response filed Jun. 25, 2013 to Final Office Action mailed Feb. 25, 2013", 8 pgs.
(Continued)

*Primary Examiner* — Ophelia A Hawthorne
*Assistant Examiner* — Michael Milo
(74) *Attorney, Agent, or Firm* — Schwegman Lundberg & Woessner, P.A.

(57) ABSTRACT

The present application relates to method and apparatus for reducing migration and rotation of implantable devices including an expandable element and an elongate portion.

19 Claims, 14 Drawing Sheets

(56) References Cited

U.S. PATENT DOCUMENTS

| | | | |
|---|---|---|---|
| 6,579,224 B1* | 6/2003 | Burton | A61F 2/004 128/DIG. 25 |
| 7,022,106 B2* | 4/2006 | Jorgensen | A61M 25/1006 604/103.09 |
| 2003/0083539 A1* | 5/2003 | Leschinsky | A61M 25/0017 600/18 |
| 2004/0186507 A1* | 9/2004 | Hall | A61M 25/10 623/1.11 |
| 2004/0215054 A1 | 10/2004 | Siegel et al. | |
| 2004/0230282 A1* | 11/2004 | Cates | A61N 1/056 607/126 |
| 2006/0129178 A1* | 6/2006 | Reifart | A61M 25/104 606/192 |
| 2007/0043255 A1* | 2/2007 | O'Donnell | A61F 2/0045 606/151 |
| 2007/0270890 A1* | 11/2007 | Miller | A61B 17/0625 606/151 |
| 2010/0292530 A1 | 11/2010 | Cook et al. | |
| 2014/0148794 A1 | 5/2014 | Cook et al. | |
| 2016/0242886 A1 | 8/2016 | Cook et al. | |
| 2017/0079762 A1 | 3/2017 | Cook et al. | |

OTHER PUBLICATIONS

"U.S. Appl. No. 12/467,257, Final Office Action mailed Feb. 25, 2013", 11 pgs.

"U.S. Appl. No. 12/467,257, Non Final Office Action mailed May 10, 2012", 7 pgs.

"U.S. Appl. No. 12/467,257, Non Final Office Action mailed Sep. 3, 2013", 8 pgs.

"U.S. Appl. No. 12/467,257, Preliminary Amendment filed Aug. 20, 2010", 3 pgs.

"U.S. Appl. No. 12/467,257, Response filed Apr. 23, 2012 to Restriction Requirement mailed Nov. 23, 2011", 7 pgs.

"U.S. Appl. No. 12/467,257, Response filed Nov. 9, 2012 to Non Final Office Action mailed May 10, 2012", 7 pgs.

"U.S. Appl. No. 12/467,257, Response filed on Jun. 25, 2013 to Final Office Action mailed Feb. 25, 2013", 8 pgs.

"U.S. Appl. No. 12/467,257, Restriction Requirement mailed Nov. 23, 2011", 7 pgs.

"U.S. Appl. No. 14/169,988, Non Final Office Action mailed Nov. 2, 2015", 9 pgs.

"U.S. Appl. No. 14/169,988, Preliminary Amendment filed Apr. 1, 2014", 4 pgs.

"U.S. Appl. No. 14/169,988, Response filed Oct. 15, 2015 to Restriction Requirement mailed May 15, 2015", 6 pgs.

"U.S. Appl. No. 14/169,988, Restriction Requirement mailed May 15, 2015", 7 pgs.

"U.S. Appl. No. 15/143,784, Non Final Office Action mailed Jul. 7, 2016", 5 pgs.

"U.S. Appl. No. 15/371,591, Non Final Office Action mailed Feb. 8, 2019", 8 pgs.

"U.S. Appl. No. 15/371,591, Preliminary Amendment filed Dec. 8, 2016", 4 pgs.

"U.S. Appl. No. 15/371,591, Response filed Jan. 28, 2019 to Restriction Requirement mailed Nov. 28, 2018", 5 pgs.

"U.S. Appl. No. 15/371,591, Restriction Requirement mailed Nov. 28, 2018", 6 pgs.

\* cited by examiner

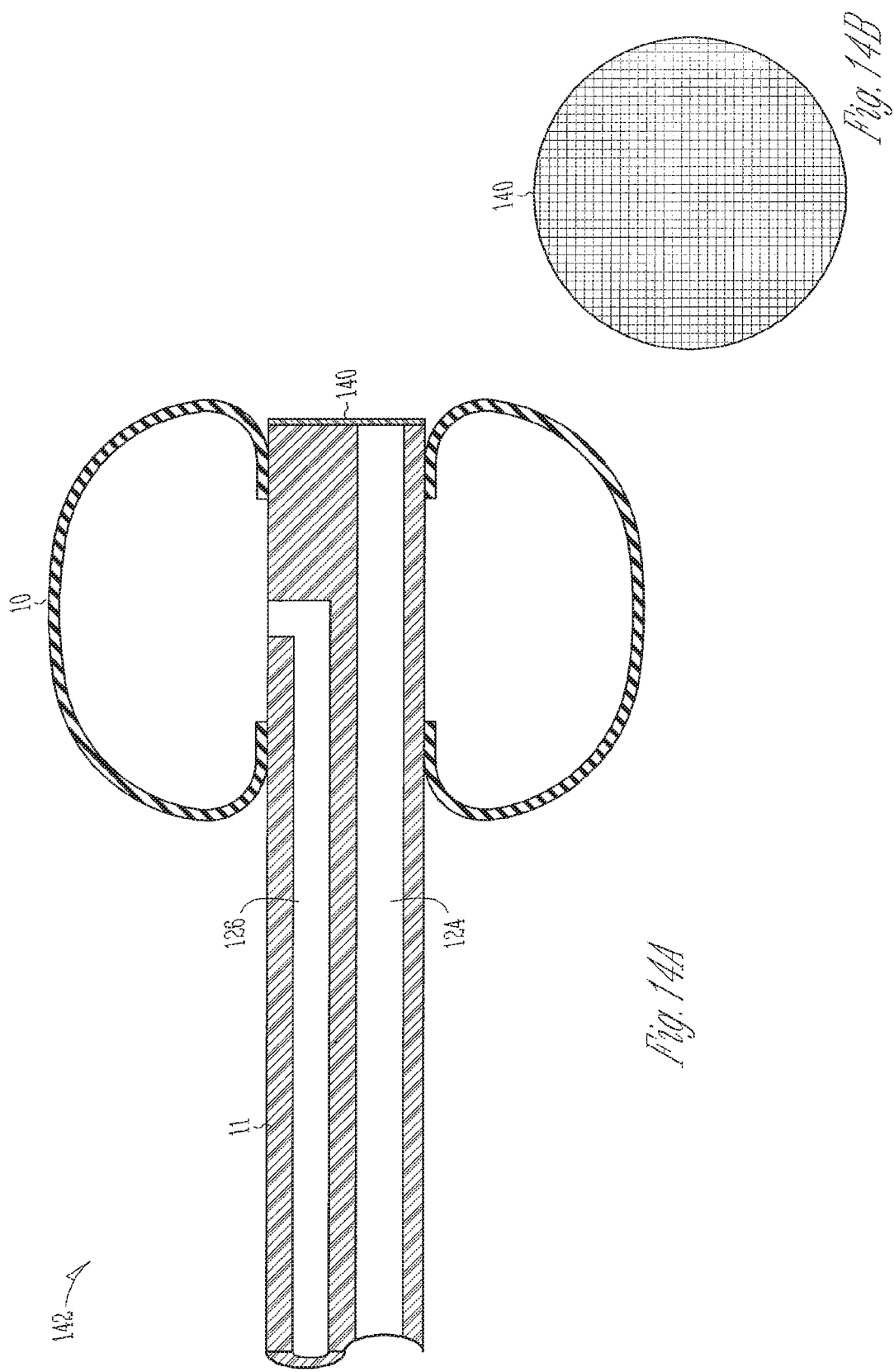

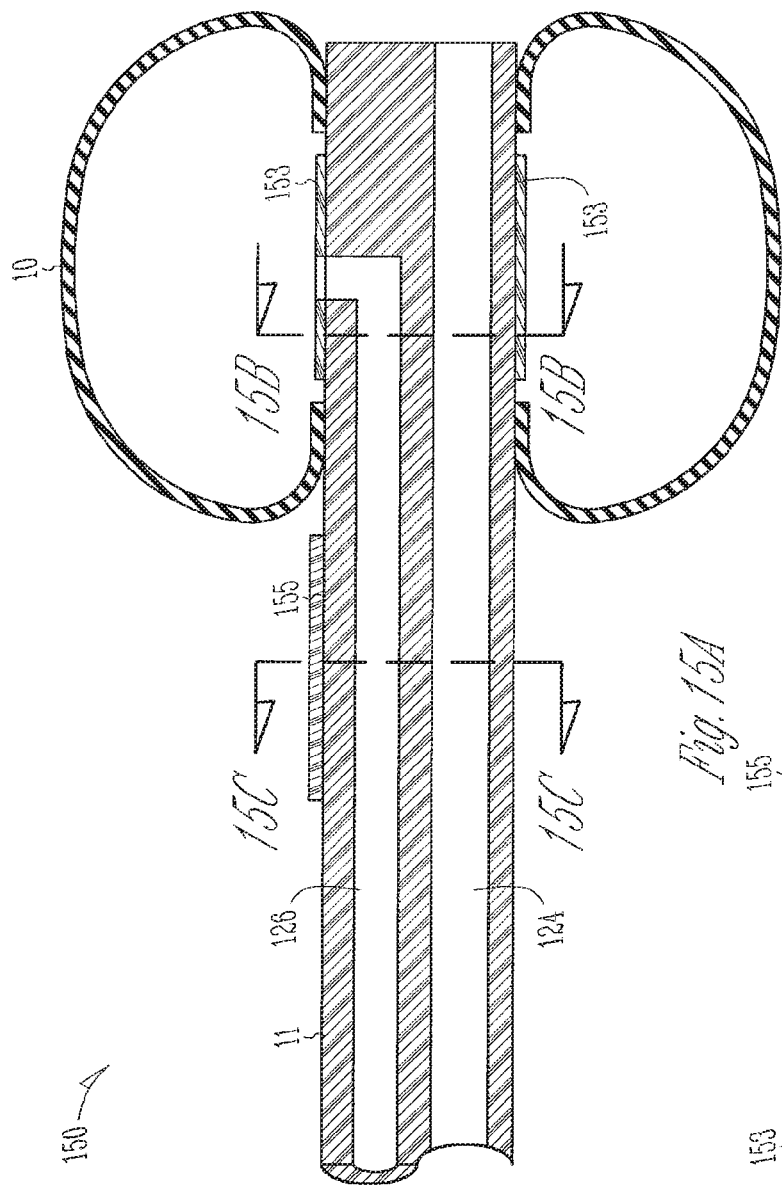

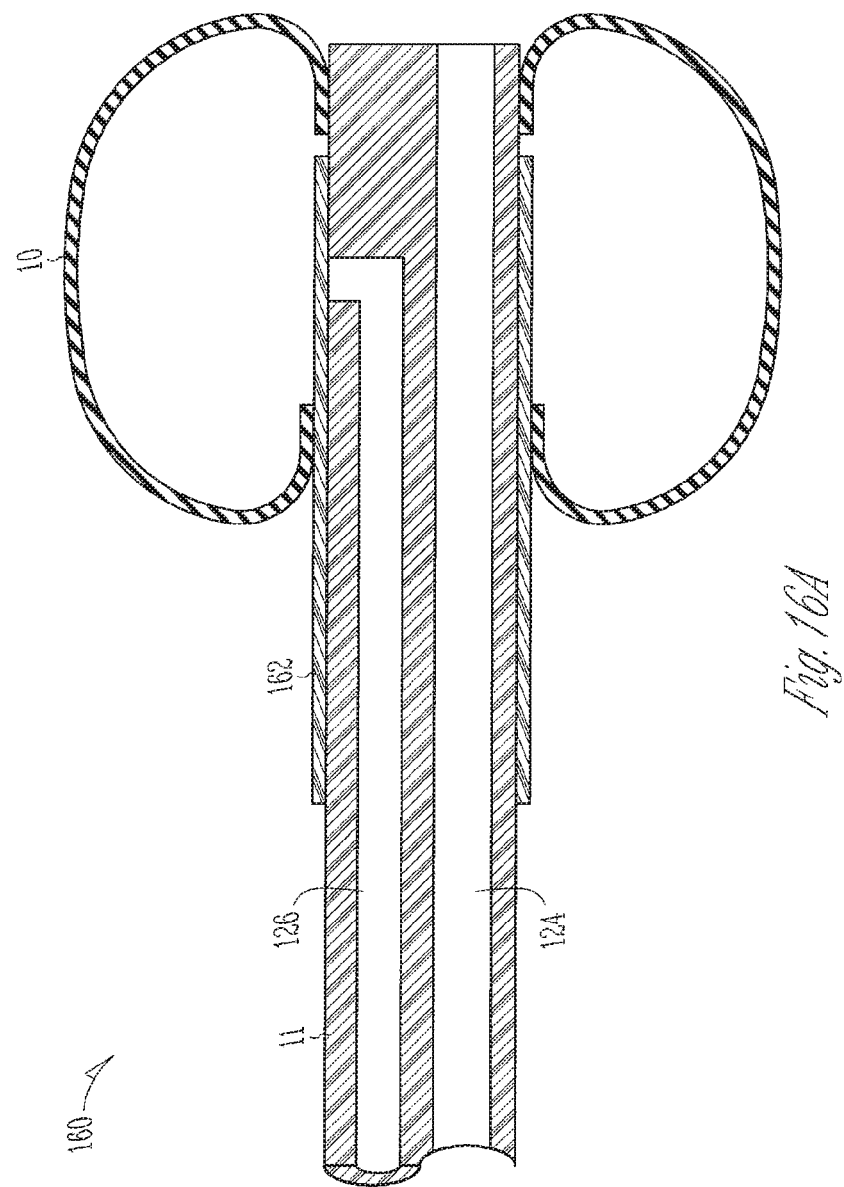

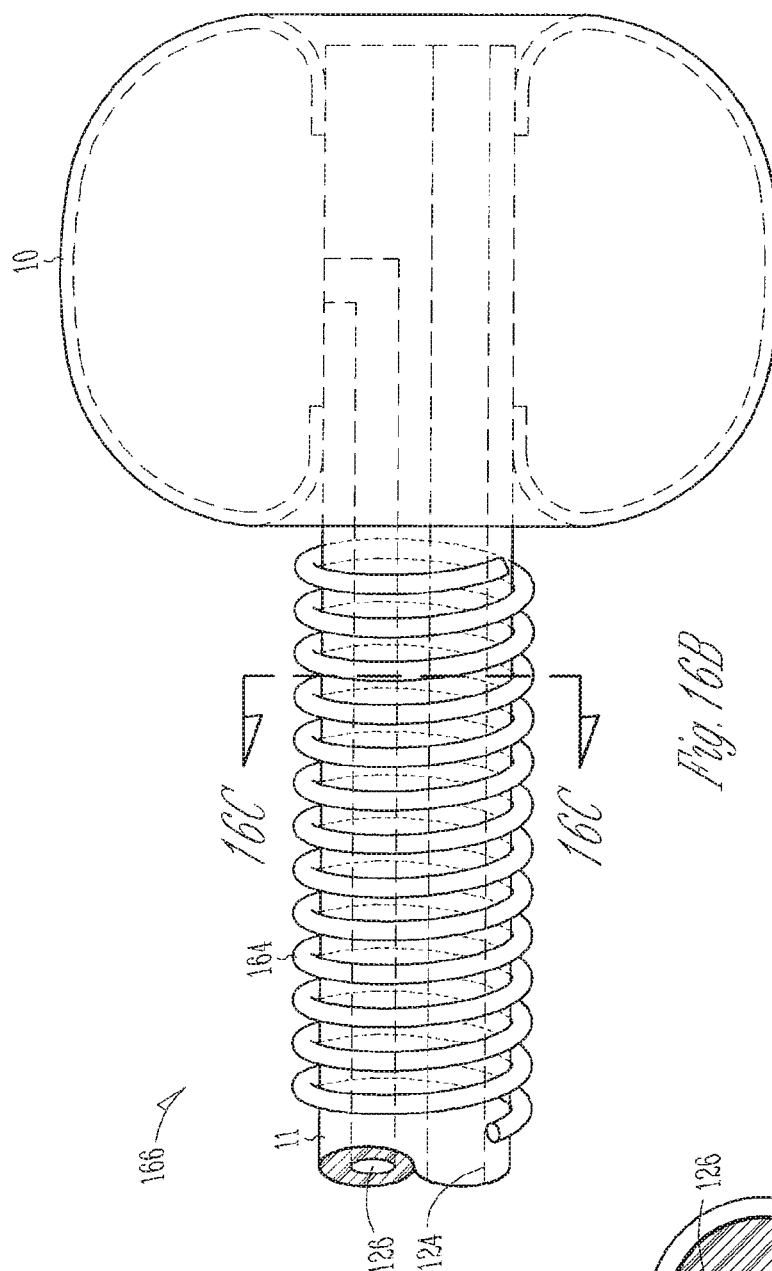
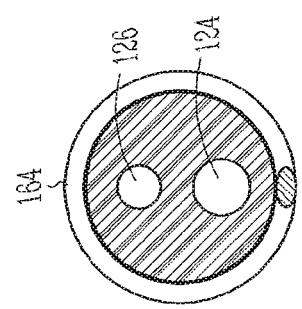
Fig. 16B
Fig. 16C

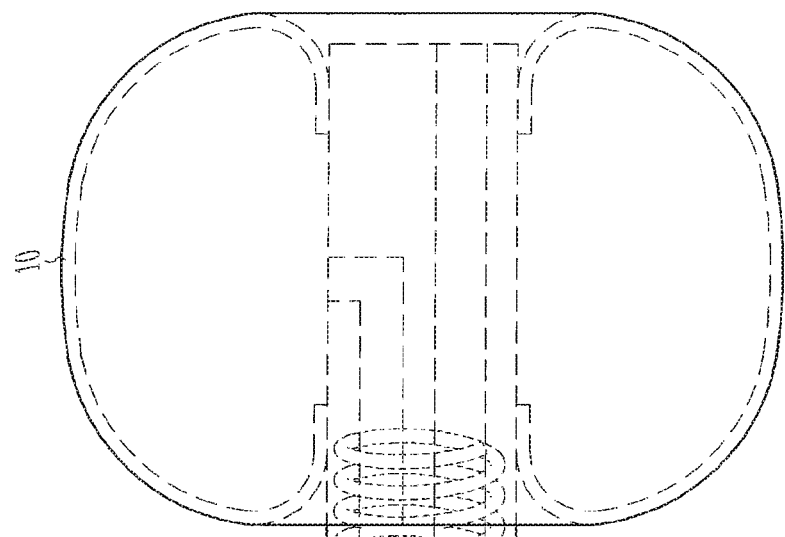
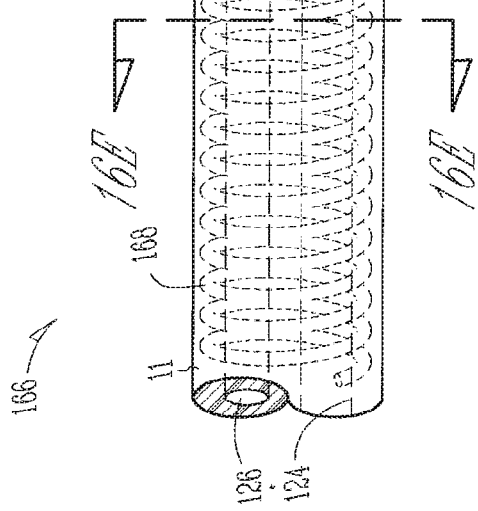
Fig. 16D
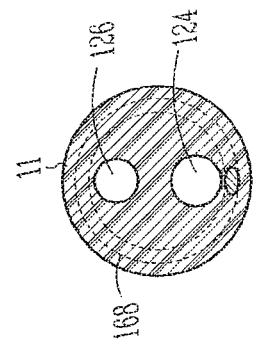
Fig. 16E

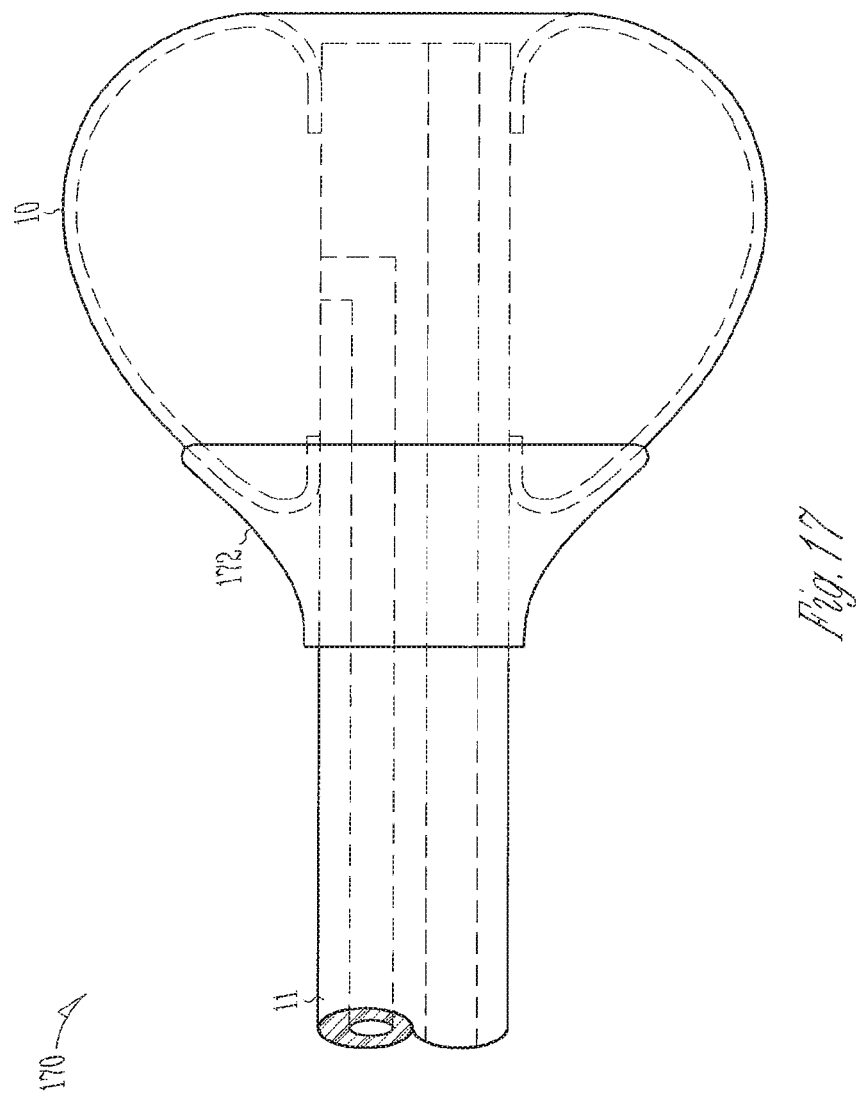

METHOD AND APPARATUS FOR FIXATION OF IMPLANTABLE DEVICES ADJACENT A BODY LUMEN

CLAIM OF PRIORITY

The present application is a continuation of U.S. patent application Ser. No. 15/371,591, filed on Dec. 7, 2016, which is a continuation of U.S. patent application Ser. No. 15/143,784, filed on May 2, 2016, which is a continuation of U.S. patent application Ser. No. 14/169,988, filed on Jan. 31, 2014, which is a continuation of U.S. patent application Ser. No. 12/467,257, filed on May 16, 2009, which claims the benefit under 35 U.S.C. 119(e) of U.S. Provisional Patent Application Ser. No. 61/053,758, filed on May 16, 2008, which applications are incorporated herein by reference in their entireties.

FIELD OF THE INVENTION

The present subject matter relates to method and apparatus for fixation of implantable devices adjacent a body lumen.

BACKGROUND

The implantation of medical devices into the tissue of patients is complicated. The surgery can be partially or wholly ineffective if the implanted devices migrate or rotate within the body after implantation. Such devices need to be removed and reimplanted if possible. Each time a device is surgically implanted or explanted, the patient suffers risks of trauma and infection, which can sometimes be lethal to the patient.

There is a need in the art for improved method and apparatus for fixation of implantable devices. Such approaches should provide an explanation option with minimal trauma to the tissue of the patient.

SUMMARY

The present application relates to method and apparatus for reducing migration and rotation of implantable devices including an expandable element and an elongate portion.

This Summary is an overview of some of the teachings of the present application and is not intended to be an exclusive or exhaustive treatment of the present subject matter. Further details about the present subject matter are found in the detailed description and the appended claims. The scope of the present invention is defined by the appended claims and their legal equivalents.

BRIEF DESCRIPTION OF THE DRAWINGS

FIGS. 14A and 14B show one example of use of ingrowth-promoting material at a distal end of an apparatus according to one embodiment of the present subject matter.

FIGS. 15A to 15E show some examples of an implantable device featuring a variable stiffness design adapted to reduce rotation according to various embodiments of the present subject matter.

FIG. 16A shows one example of an external stiffener for an implantable device according to one embodiment of the present subject matter.

FIGS. 16B and 16C show one example of an externally coiled stiffener for an implantable device according to one embodiment of the present subject matter.

FIGS. 16D and 16E show different examples of an internally coiled stiffener for an implantable device according to various embodiments of the present subject matter.

FIG. 17 shows one example of a restraint on a proximal bond according to one embodiment of the present subject matter.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to implantable devices which can be placed near a patient's urethra to improve continence. The implantable devices are described in applications such as such as the implantable devices described in U.S. Pat. Nos. 6,045,498, 5,964,806, 6,579,224, and 6,419,624 and their related patents and applications, the description; of which are hereby incorporated in their entirety. Such applications also contain information as to the placement of the implantable devices. Placement of such devices is also discussed in U.S. Provisional Patent Application Ser. No. 61/039,738, filed Mar. 26, 2008, entitled: METHOD AND APPARATUS FOR PLACEMENT OF IMPLANTABLE DEVICE ADJACENT A BODY LUMEN, which is incorporated by reference in its entirety.

Figure 1A:
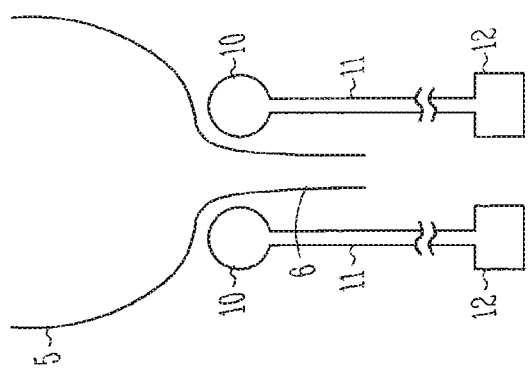
FIG. 1A shows an example of placement of implantable devices with respect to a human bladder and urethra according to one embodiment of the present subject matter.

FIG. 1A shows an example of placement of implantable devices with respect to a human bladder and urethra according to one embodiment of the present subject matter. In one embodiment of the implantable devices, an expandable element 10 is connected to an elongate conduit 11 and terminates in a port 12, such as a septum. Typically, the expandable element 10 is implanted proximal the urethra 6 near the bladder 5. Such location is also referred to as the "bladder neck." The actual positions of the expandable elements 10 of such devices with respect to the urethra 6 and bladder neck may vary; however, FIG. 1A shows the original position of the devices compared to the positions in FIGS. 1B and 1C for purposes of demonstration of the unwanted aspects of migration and rotation.

Figure 1B:
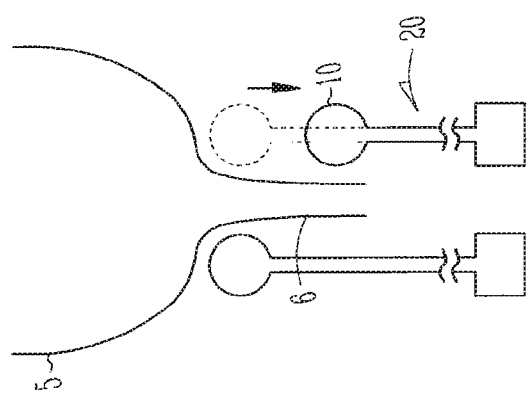
FIG. 1B demonstrates migration of one of the two implantable devices.

FIG. 1B demonstrates migration of one of the two implantable devices. Some time after implantation, it is possible to find that the expandable element 10 of implantable device 20 has moved from its original implantation site. In some cases the expandable element 10 will move down the dilation tract formed during implantation of the device. Once it has moved out of position, the implantation may no longer provide adequate tissue bulking in the vicinity of the bladder neck, and may fail to restore continence as needed.

Figure 1C:
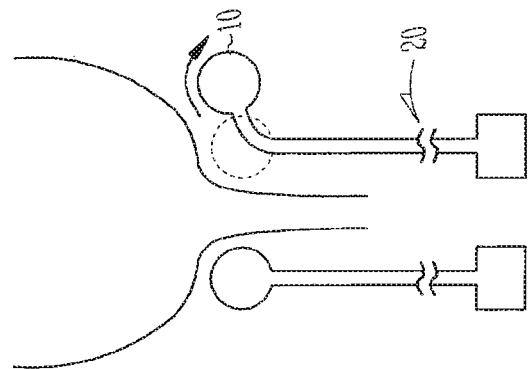
FIG. 1C demonstrates rotation of one expandable element of one of the two implantable devices.

Another unwanted effect that may be possible to find is rotation. FIG. 1C demonstrates rotation of one expandable element of one of the two implantable devices. The expandable element 10 of implantable device 20 is shown as being rotated in position relative to its original placement. The rotation can result in displacement of the expandable element 10, which may reduce the efficacy of the implantation for purposes of enhancing coaptation, and continence. However, rotation can be problematic even in cases where the expandable element 10 is not substantially displaced because the elongate conduit 11 can apply unwanted force on the expandable element 10 and may result in device failure over time due to erosion of material.

Figure 2:
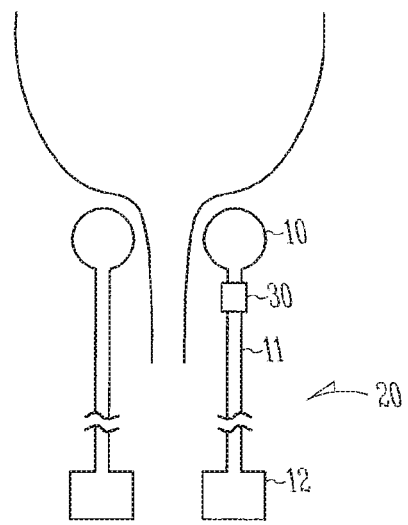
FIG. 2 shows placement of a sleeve adapted to provide ingrowth to provide an adhesion according to one embodiment of the present subject matter.
Figure 3:
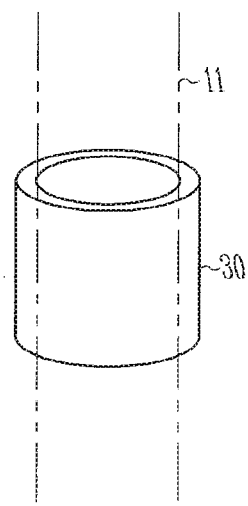
FIG. 3 shows a closeup of the sleeve of FIG. 2.

One way to reduce the chances of movement of the expandable element 10 after implantation is to provide a means for adhesion of the implantable device to the tissue in which it is implanted. FIG. 2 shows placement of a sleeve adapted to provide ingrowth to provide an adhesion according to one embodiment of the present subject matter. In one embodiment a small adhesion forms near the end of the tubing closest to the expandable element 10 by the use of an ingrowth collar or sleeve 30. Different materials can be used, including but not limited to EPTFE (expanded polytetrafluoroethelene as used in some vascular grafts) to encircle the elongate conduit 11 near the expandable element 10. The ingrowth collar or sleeve 30 allows the adhesion to form which is a form of fixation of the device to avoid migration and to avoid rotation. Other ingrowth materials may include polypropylene or polyethylene mesh as used for hernia repairs or open cell silicone or polyurethane foams. In various embodiments it is beneficial to use a mesh or foam cell size and/or material and/or surface area selected to make the adhesion of limited strength so that the implantable device 20 can be pulled out without breaking it during removal or causing trauma to surrounding tissue. In one embodiment, the ingrowth sleeve 30 as designed to have less than a 5 lb. pull strength. Other pull strength limits are possible without departing from the scope of the present subject matter. FIG. 3 shows a closeup of the sleeve of FIG. 2, which is friction fit or otherwise secured to the elongate conduit 11 of the implantable device 20 in various embodiments. In certain embodiments the ingrowth material is bioresorbable so that it fixes the device in place after a short time allowing the surrounding tissue to adapt and stabilize the device but would be resorbed over a longer timeframe and allow the device to be easily removed if need be. One example of a bioresorbable material is polylactic acid.

In one embodiment, the implantable device 20 can be removed by cutting off the septum, feeding a cylindrical tool over the implantable device, and using the tool to go over the conduit, cutting the adhesion to facilitate removal of the implantable device at a pull strength that is less than what would destroy the implantable device. The cylindrical tool may also have a slot along its length so that it can be fit over and along the conduit so that the part need not be cut off. In various embodiments, the tool can cut between the elongate conduit and the sleeve or the tool can cut the sleeve away from the tissue. One type of tool to accomplish the cutting is the use of a properly positioned beveled blade. Other tools and approaches are possible without departing from the scope of the present subject matter.

Figure 4:
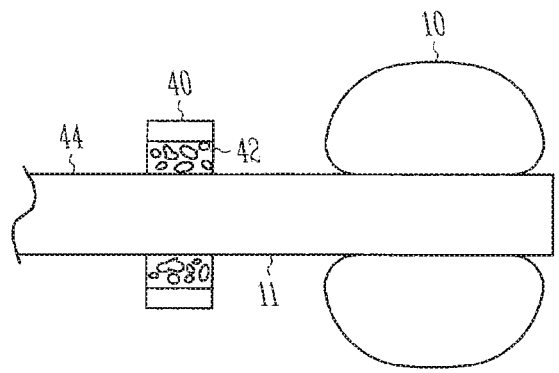
FIG. 4 shows a cross section of an implantable device including a sleeve attached using an adhesive according to one embodiment of the present subject matter.
Figure 10:
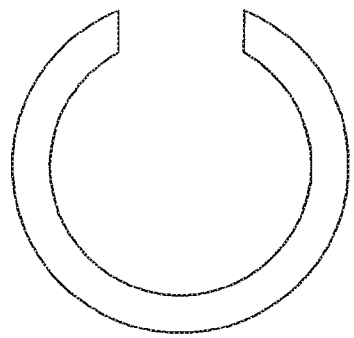
FIG. 10 shows one example of a split ring device adapted to enhance ingrowth according to one embodiment of the present subject matter.
Figure 11:
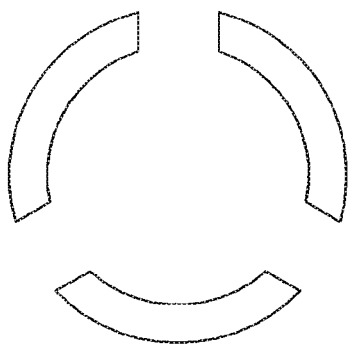
FIG. 11 shows one example of a segmented ring device adapted to enhance ingrowth according to one embodiment of the present subject matter.

FIG. 4 shows a cross section of an implantable device 44 including a sleeve 40 attached to elongate conduit 11 using an adhesive 42 according to one embodiment of the present subject matter. Such sleeves 40 provide adequate fixation of the implantable device 44 during its implantation. In such embodiments, the adhesive has a tear strength which is less than the pull strength limit of the implantable device 44. Thus, to remove the implantable device 44, the sleeve 40 may stay in place while the glue 42 shears as the implantable device 44 is pulled out of the patient. In such embodiments, the split ring or segmented ring sleeves as shown in FIGS. 10 and 11 may be used to allow the withdrawal of the implantable device. This is especially useful for devices where the cross section at the expandable element 10 is greater than the cross section for the elongate conduit 11. Other types of split ring sleeves may be used without departing from the scope of the present subject matter.

Figure 5:
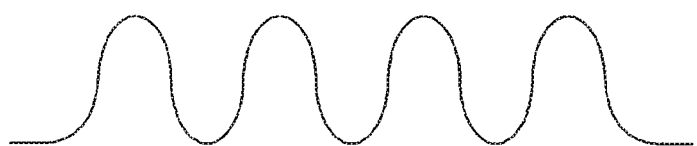
FIG. 5 shows a cross section of surface structure adapted to enhance ingrowth according to one embodiment of the present subject matter.

FIG. 5 shows a cross section of surface structure adapted to enhance ingrowth according to one embodiment of the present subject matter. The surface structure can be porous and is selected to provide the proper pull strength, yet retain the implantable device in position during its normal use.

Figure 6:
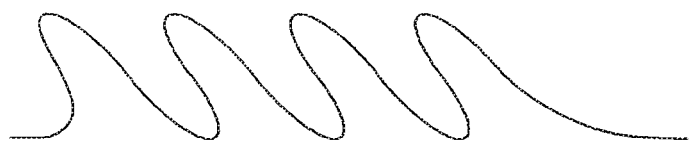
FIG. 6 shows a cross section of surface structure adapted to enhance ingrowth and resist migration according to one embodiment of the present subject matter.

FIG. 6 shows a cross section of surface structure adapted to enhance ingrowth and resist migration according to one embodiment of the present subject matter. The angled nature of the structure forms additional resistance to migrations back down the dialation path.

Figure 7:
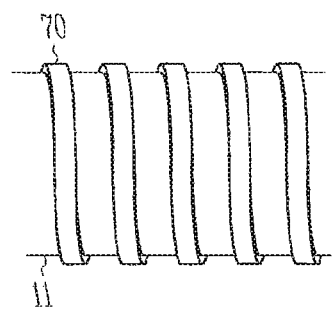
FIG. 7 shows a cross section of a helical sleeve structure adapted to enhance ingrowth according to one embodiment of the present subject matter.
Figure 8:
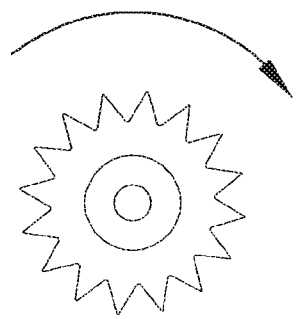
FIG. 8 shows one example of a tool for removal of a helical sleeve structure according to one embodiment of the present subject matter.

FIG. 7 shows a cross section of a helical sleeve structure adapted to enhance ingrowth according to one embodiment of the present subject matter. The helical sleeve structure 70 over the elongate conduit 11 acts to fix the implantable device. To remove the device, it is screwed out of the tissue. In one embodiment a pushwire or other rod is used to withdraw the device. The pushwire or rod can be keyed to facilitate application of torque to withdraw the device. In one embodiment, a structure, such as that shown in FIG. 8, is used to lock the pushwire or rod with a channel or other receiver in the implantable device for withdrawal. FIG. 8 shows one example of a tool for removal of a helical sleeve structure according to one embodiment of the present subject matter.

Figure 9:
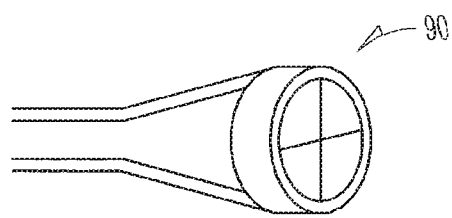
FIG. 9 shows one example of an expandable tool for removal of a helical sleeve structure according to one embodiment of the present subject matter.

In various embodiments a collet-type device, such as the expanding device shown in FIG. 9 is used to withdraw the device. FIG. 9 shows one example of an expandable tool for removal of a helical sleeve structure according to one embodiment of the present subject matter. A remote actuator (not shown) is used to expand distal ring 90 so as to engage with a lumen or other feature of the implantable device which is to be extracted.

Figures 12A, 12B:
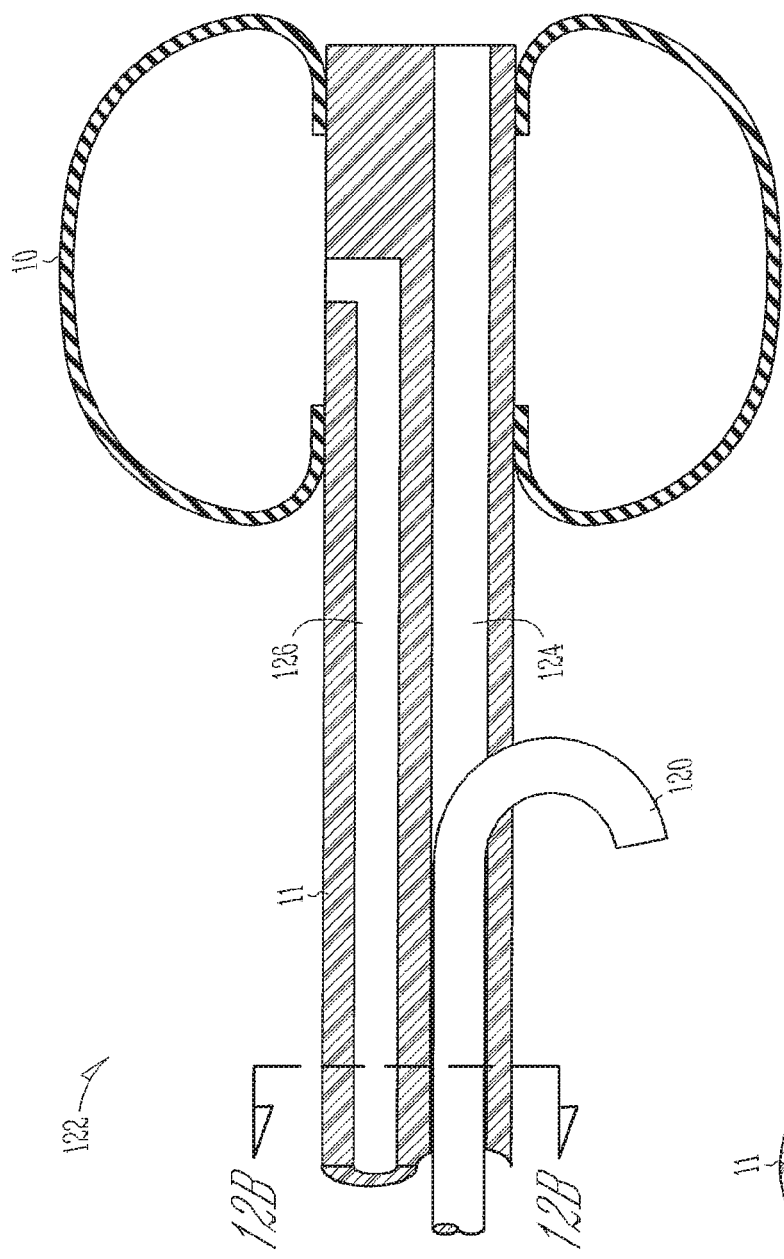
FIG. 12A shows one example of a hook adapted for fixation according to one embodiment of the present subject matter.
FIG. 12B shows a cross section of a portion of the implantable device of FIG. 12A according to one embodiment of the present subject matter.

FIG. 12A shows one example of a hook adapted for fixation according to one embodiment of the present subject matter. In one embodiment, after the implantable device 122 is placed in position, a Nitinol hook 120 is threaded through an inner lumen 124 of the elongate conduit 11 of implantable device 122 and exits the inner lumen 124 from an exit on the elongate conduit 11 to serve as a fixation to the local tissue. The exit is proximal to the expandable element 10 of the implantable device 122. Other types of hooks may be used without departing from the scope of the present subject matter. The hook is placed near the expandable element 10 of the implantable device 122 to retain it in position. FIG. 12B shows a cross section of elongate conduit showing a cross section of hook 120 in the space of what was the inner lumen 124 and another inner lumen 126 in communication with expandable element 10. In various embodiments inner lumen 126 is connected to a port with a septum (not shown) as described in the various documents incorporated by reference. In various embodiments inner lumen 124 is used with various implantation tools such as a pushrod or other tool to place implantable device 122 in position. Various inner lumens for implantable devices are described in patent documents, including, but not limited to, U.S. Pat. Nos. 6,045,498, 5,964,806, 6,579,224, and 6,419,624 and their related patents and applications, the descriptions of which are hereby incorporated in their entirety. Such applications also contain information as to the placement of the implantable devices. Placement of devices is discussed in various documents, including, but not limited to U.S. Provisional Patent Application Ser. No. 61/039,738, filed Mar. 26, 2008, entitled: METHOD AND APPARATUS FOR PLACEMENT OF IMPLANTABLE DEVICE ADJACENT A BODY LUMEN, which is incorporated by reference in its entirety.

Figure 13:
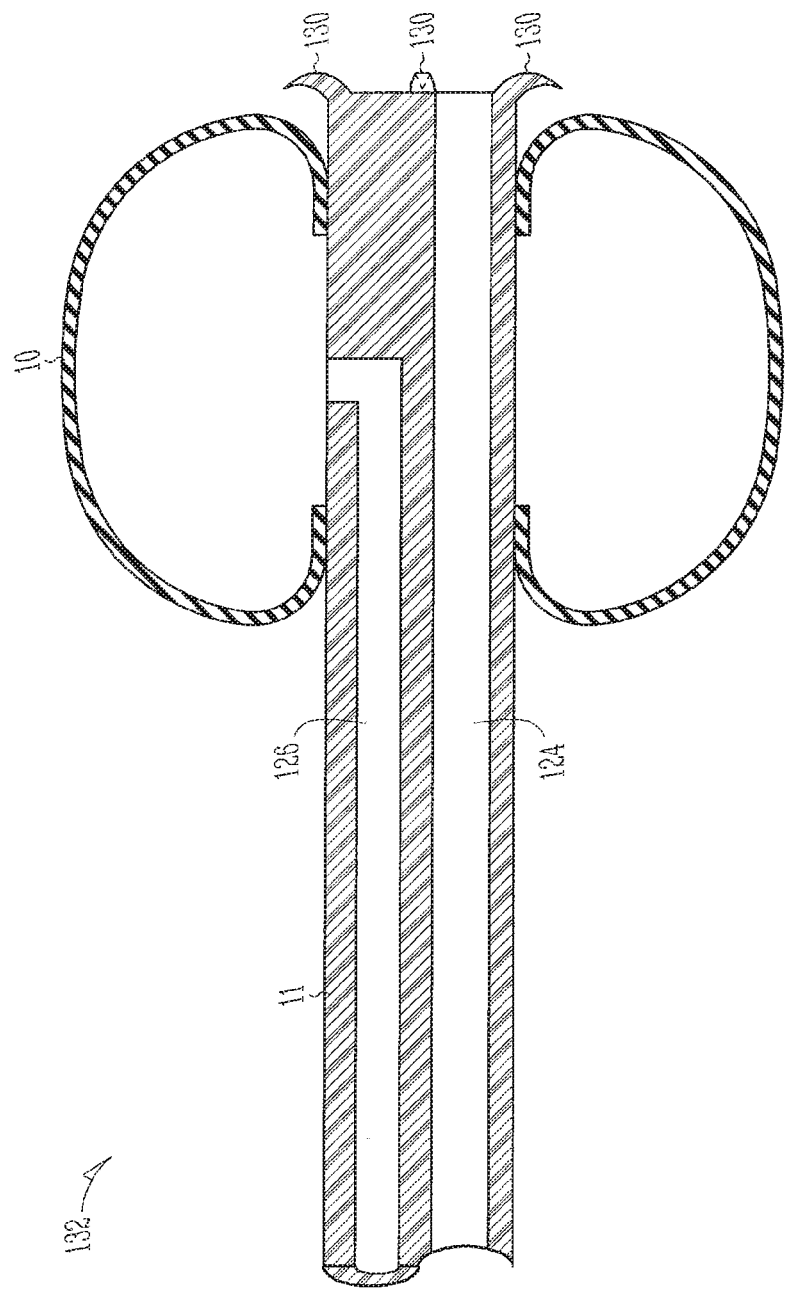
FIG. 13 shows one example of a plurality of hooks adapted for fixation according to one embodiment of the present subject matter.

FIG. 13 shows one example of a plurality of hooks adapted for fixation according to one embodiment of the present subject matter. In various embodiments, fixation hooks 130 at the distal tip of the elongate conduit 11 are deployed to provide fixation to the tissue after the implantable device 132 is placed in its desired position. In various embodiments, the expandable element 10 is expanded and the hooks 130 are recessed to shield bladder from puncturing. Other hook positions, shapes, and numbers are possible without departing from the scope of the present subject matter.

FIGS. 14A and 14B show one example of use of ingrowth-promoting material at a distal end of an implantable device according to one embodiment of the present subject matter. In various embodiments, a patch or coating of ingrowth-promoting material 140 at the distal end of the device 142 provides adhesion at or near the distal end of the device 142. Such approaches can reduce migration and rotation of expandable element 10. In certain embodiments the ingrowth material is bioresorbable so that it fixes the device in place after a short time allowing the surrounding tissue to adapt and stabilize the device but would be resorbed over a longer timeframe and allow the device to be easily removed if need be. One example of a bioresorbable material is polylactic acid. It is understood that various materials, shapes and positions can be used without departing from the scope of the present subject matter.

FIGS. 15A-E show some examples of an implantable device featuring a variable stiffness design adapted to reduce rotation according to various embodiments of the present subject matter. In FIG. 15A different stiffeners are shown, which may be used individually, or in combination, in various applications. FIG. 15B is a cross section drawing showing stiffener 153 which is a form of annular ring with an aperture for filling expandable element 10. FIG. 15C is a cross section showing a stiffening member 155 FIG. 15D shows a cross section showing a separate lumen with a stiffening member 157. FIG. 15E shows a cross section with an annular stiffening member 159 placed in inner lumen 124. In some embodiments, expansion of the expandable element 10 can also make tubing in central portion stretch and can also have a preferential force on the tubing and may cause it to rotate. In various embodiments a stiffener of varying stiffness can he inserted in a lumen of the elongate conduit to provide more stiffening at the distal end than at the proximal end of the implantable device 150. In one application, a stiffener 157 is added to a third central lumen of the implantable device after it is deployed into position. In varying embodiments, the stiffening effect is built into the implantable device as it is manufactured. In various embodiments, a stiffener 159 is placed in the same lumen 124 that is used to position the implantable device. This could be done by the surgeon after removing the pushwire at time of implant. Other types of stiffeners and deployments are possible without departing from the scope of the present subject matter.

FIG. 16A shows one example of an external stiffener for an implantable device according to one embodiment of the present subject matter. In such embodiments, sleeve 162 provides additional stiffness at the proximal bond area of elongate conduit 11 of the expandable element 10. In various embodiments, the sleeve 162 continues into the expandable element 10 portion of the elongate conduit 11. In various embodiments the sleeve 162 is manufactured as an integral portion of elongate conduit 11.

In various embodiments, a lubricious coating, sleeve, or material can be positioned anywhere along the elongate conduit or about the external stiffener in embodiments which employ a stiffener, or both, to reduce or eliminate wear should the expandable element 10 come in contact with the stiffener and/or the elongate conduit. In such events, the lubricious coating, sleeve, or material would prevent wear of the expandable element 10.

FIGS. 16B and 16C show one example of an externally coiled stiffener for an implantable device according to one embodiment of the present subject matter. As shown in FIGS. 16B and 16C, coil 164 can be placed outside of elongate conduit 11. A coil can also be disposed within the elongate conduit 11 as shown as coil 168 in FIGS. 16D and 16E. Coils 164 and 168 provide additional stiffness to prevent rotation of the expandable element 10 of implantable device 166.

FIG. 17 shows one example of a restraint on a proximal bond according to one embodiment of the present subject matter. The restraint 172 on the proximal bond of the expandable element 10 to elongate conduit 11 reduces or eliminates wear and/or erosion on the proximal bond. In various embodiments, the restraint 172 is a collar that is attached to the implantable device 170. In various embodiments, the restraint 172 is generated by one or more additional dips in the coating process that produces the implantable device 170. In various embodiments, the restraint provides asymmetric balloon inflation of the expandable element 10. Other shapes and constraints and asymmetries are possible without departing from the scope of the present subject matter.

Expandable elements with asymmetrical shapes can be engineered to reduce the possibility of contact with the elongate conduit by the expandable element. For example, the bulge shown in the example of FIG. 17 is larger at the distal end of the expandable element, which can reduce the tendency of the expandable element to come in contact with the elongate conduit.

Figure 18A:
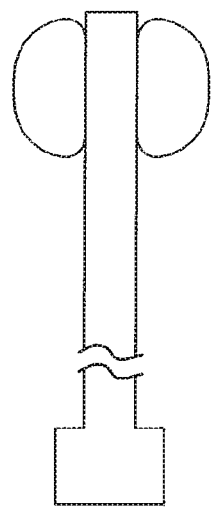
FIG. 18A shows one embodiment of an irregular shape of an expandable element of the implantable device according to one embodiment of the present subject matter, as compared to that of FIG. 18B.
Figure 18B:
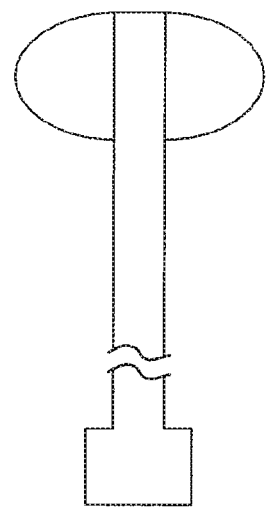

FIG. 18A shows one embodiment of an irregular shape of an expandable element of the implantable device according to one embodiment of the present subject matter, as compared to that of FIG. 18B. The irregular shape is made squarer than that of FIG. 18B to avoid rotation. Various different shapes may be used without departing from the scope of the present subject matter.

Figure 19:
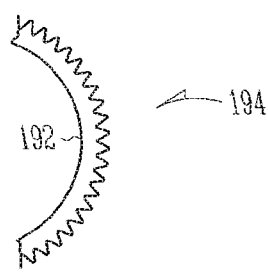
FIG. 19 shows one embodiment of a microtextured expandable element according to one embodiment of the present subject matter.

FIG. 19 shows one embodiment of a microtextured expandable element according to one embodiment of the present subject matter. A portion of the wall of expandable element 192 is microtextured 194 to reduce rotation. A tool can be employed to remove the expandable element 10.

Figure 20:
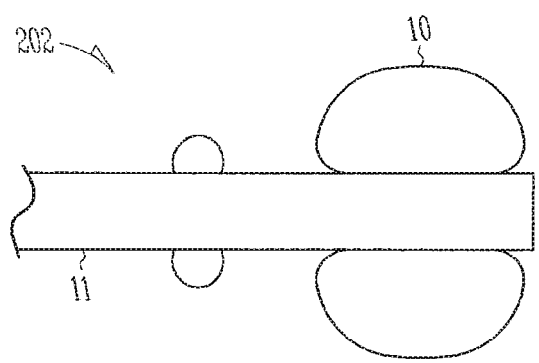
FIG. 20 shows one embodiment of an extra stabilizing balloon for an implantable device according to one embodiment of the present subject matter.

FIG. 20 shows one embodiment of an extra stabilizing balloon for an implantable device according to one embodiment of the present subject matter. Balloon 202 is placed to prevent the implantable device from migrating, and may avoid rotation by holding the elongate conduit in place and thereby limit the expandable element 10 from rotating.

It is understood that various combinations of the foregoing aspects of the present subject matter can be combined to provide apparatus having multiple benefits.

This application is intended to cover adaptations and variations of the present subject matter. it is to be understood that the above description is intended to be illustrative, and not restrictive. The scope of the present subject matter should be determined with reference to the appended claim, along with the full scope of legal equivalents to which the claims are entitled.

What is claimed is:

1. An implantable device for implantation into tissue adjacent to an urethra connected to a bladder, comprising: an expandable balloon capable of expansion in the tissue adjacent to the urethra connected to an elongate conduit, the elongate conduit configured to provide for a plurality of lumens including a first inner lumen for fluid communication between a first end of the elongate conduit at a proximal portion of the implantable device and the expandable balloon at a second end at a distal portion of the implantable device and a second inner lumen; and a plurality of distal hooks positioned at a distal tip of the elongate conduit to be deployed distally to the expandable balloon, wherein the implantable device is configured for implantation within the tissue with the expandable balloon adjacent the urethra for adjustable coaptation to the urethra, wherein the plurality of distal deployable hooks is configured to be deployed into the tissue adjacent the urethra after positioning the implantable device to provide fixation of the implantable device in the tissue adjacent the urethra, wherein the expandable balloon and the plurality of distal hooks are arranged for the expandable balloon to shield the bladder from being punctured by the plurality of distal hooks positioned at the distal tip of the elongate conduit when the expandable balloon is expanded, and wherein a stiffener comprising an aperture for filling the expandable balloon is disposed onto an expandable balloon portion of the elongate conduit.

2. The implantable device of claim 1, further comprising a sleeve positioned about the elongate conduit, the sleeve configured to avoid migration and rotation of the implantable device in the tissue.

3. The implantable device of claim 2, wherein the sleeve is bioresorbable.

4. The implantable device of claim 3, wherein the sleeve comprises polylactic acid.

5. The implantable device of claim 2, wherein the sleeve is attached to the elongate conduit using an adhesive.

6. The implantable device of claim 5, wherein the adhesive has a tear strength less than a pull strength limit of the implantable device to allow the implantable device to be pulled out of the tissue while the sleeve stays in the tissue.

7. The implantable device of claim 2, wherein the sleeve is positioned on the elongate conduit near the expandable balloon.

8. The implantable device of claim 2, wherein the sleeve comprises expanded polytetrafluoroethelene (EPTFE).

9. The implantable device of claim 2, wherein the sleeve comprises polypropylene.

10. The implantable device of claim 2, wherein the sleeve comprises polyethylene.

11. The implantable device of claim 2, wherein the sleeve comprises a split ring.

12. The implantable device of claim 2, wherein the sleeve comprises a segmented ring.

13. The implantable device of claim 2, wherein the sleeve comprises a helical sleeve.

14. The implantable device of claim 1, wherein the expandable balloon is microtextured to reduce rotation in the tissue.

15. The implantable device of claim 1, wherein the second inner lumen is employed to position the implantable device.

16. The implantable device of claim 15, further comprising a pushrod configured to be used in the second inner lumen to place the implantable device in position.

17. A method of treating incontinence in a human using tissue adjacent a urethra of the human connected to a bladder of the human, comprising: introducing to the tissue adjacent to a urethra of the human an implantable device including an expandable balloon capable of expansion in the tissue adjacent to the urethra connected to an elongate conduit, the elongate conduit configured to provide for a plurality of lumens including a first inner lumen for fluid communication between a first end of the elongate conduit at a proximal portion of the implantable device and the expandable balloon at a second end at a distal portion of the implantable device and a second inner lumen; positioning the expandable balloon relative to the bladder and urethra of the human; deploying a plurality of distal hooks into the tissue adjacent the urethra after positioning the implantable device to provide fixation of the implantable device in the tissue adjacent the urethra, the plurality of distal hooks positioned at a distal tip of the elongate conduit to be deployed distally to the expandable balloon; and expanding the expandable balloon to shield the bladder from being punctured by the plurality of distal hooks at the distal tip of the elongate conduit, wherein the implantable device is configured for implantation within the tissue with the expandable balloon adjacent the urethra for adjustable coaptation to the urethra, and wherein a stiffener comprising an aperture for filling the expandable balloon is disposed onto an expandable balloon portion of the elongate conduit.

18. The method of claim 17, wherein the second inner lumen is employed to position the implantable device.

19. The method of claim 18, further comprising using a pushrod in the second inner lumen to place the implantable device in position.

\* \* \* \* \*